United States Patent [19]

Speranza et al.

[11] Patent Number: 4,996,315

[45] Date of Patent: Feb. 26, 1991

[54] SYNTHESIS OF CYCLIC COMPOUNDS

[75] Inventors: George P. Speranza, Austin; Jiang-Jen Lin, Houston, both of Tex.

[73] Assignee: Texaco Chemical Company, White Plains, N.Y.

[21] Appl. No.: 465,682

[22] Filed: Jan. 16, 1990

[51] Int. Cl.$^5$ .............................................. C07D 269/00
[52] U.S. Cl. ..................................... 540/454; 540/488
[58] Field of Search ................................ 540/454, 488

[56] References Cited

U.S. PATENT DOCUMENTS

| | | | |
|---|---|---|---|
| 3,452,002 | 6/1969 | Brasch | 540/454 |
| 4,487,928 | 12/1984 | Richter et al. | 544/193 |

OTHER PUBLICATIONS

C. J. Pedersen, "Cyclic Polyethers and Their Complexes with Metal Salts," *Journal of the American Chemical Society*, vol. 89, No. 10, May 10, 1967, pp. 2495-2496.

C. J. Pedersen, "Cyclic Polyethers and Their Complexes with Metal Salts," *Journal of the American Chemical Society*, vol. 89, No. 26, Dec. 20, 1967, pp. 7017-7036.

D. J. Brunelle et al., "Preparation and Polymerization of Cyclic Oligomeric Carbonates: New Route to Super-High Molecular Weight Polycarbonate: An Overview," *Polymer Preprints*, vol. 30, No. 2, Sep. 1989, pp. 569-570.

*Primary Examiner*—Robert T. Bond
*Attorney, Agent, or Firm*—Jack H. Park; Kenneth R. Priem; David L. Mossman

[57] ABSTRACT

Novel cyclic ester-amides having the formula:

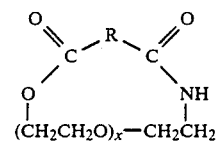

where R is an alkyl group having from 2 to 5 carbon atoms, and x ranges from 2 to 6 by reacting a polyethylene glycol monoamine having the formula $NH_2$—$(CH_2CH_2O)_x$—H, where x is as above, with at least one dicarboxylic acid, where the dicarboxylic acid is selected from the group consisting of glutaric, adipic, pimelic acids and mixtures thereof. The a molar ratio of polyethylene glycol monoamine to dicarboxylic acid should be about 1:1. Catalysts may be optionally used, and may include such compounds as titanium alkoxides; and zinc, manganese and antimony salts of carboxylic acids. This method is anticipated to be a useful step in a new preparation of valuable cyclic products.

18 Claims, No Drawings

SYNTHESIS OF CYCLIC COMPOUNDS

CROSS-REFERENCES TO RELATED APPLICATIONS

This application is related to U.S. Pat. application Ser. No. 07/465,666, filed of even date, relating to novel bis-hydroxy diamides and methods for making them.

FIELD OF THE INVENTION

The invention relates to by-products from the manufacture of polyoxyalkyleneamines, and, in one aspect, more particularly relates to the preparation of cyclic ester-amides by the reaction of dibasic acid with polyethylene glycol monoamine.

BACKGROUND OF THE INVENTION

The preparation of cyclic materials is receiving more attention. A recent study involving the synthesis of cyclic oligomeric carbonates and their polymerization to high molecular weight polycarbonates is noteworthy: D. J. Brunelle, et al., ACS, *Polymer Preprints*, Vol. 30, No. 2, 1989, Miami Beach, Fla. Because the cyclic oligomeric products have relatively low molecular weights and viscosities, they are very suitable for molding applications and other reactive processing techniques. The advantages of "cyclics" technology in the preparation of thermoplastic composites is described in *Modern Plastics*, Nov. 1989, p. 10.

Another class of cyclic materials which has received considerable attention for over twenty years is the large ring cyclic compounds. In 1967, Pederson described his pioneering work on the synthesis of macrocyclic polyethers; Pedersen, C. J., *Journal of the American Chemical Society*, Vol. 89, p. 2495 and p. 7017, 1967. These cyclic crown ethers (I) were capable of forming surprisingly stable complexes with alkali and alkaline earth metal cations. The preparations of these "simple" cyclic products was followed by the preparation of other cyclic products having sulfur or nitrogen as donor atoms (II). Monocyclics were succeeded by bicyclic compounds (III) called cryptands.

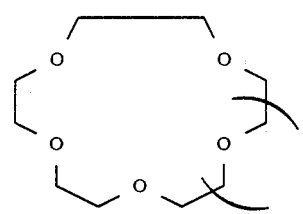

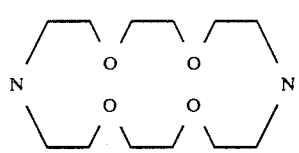

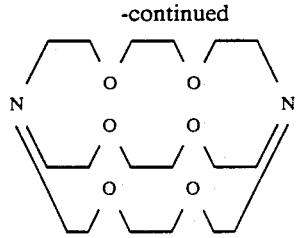

The scientific and practical interest in complexing cations by crown compounds is increasing—over 250 original papers dealing with crown ethers appeared in 1980 alone.

The unique ability of crown ethers to form stable complexes with various cations has been used in such processes as metal separation, transfer catalysts, increasing the activity of catalysts, solubilizing sodium and potassium carbonate in apolar solvents such as benzene, and catalysis of isocyanates to isocyanurates, see U.S. Pat. No. 4,487,928.

One of the main drawbacks in the use of crown compounds in industrial synthetic work is their cost due to the tedious methods needed for their preparation. High dilution techniques utilizing the "template" route is still the best way. Such routes not only use expensive reagents, but the yields are low and low volume production adds to the costs.

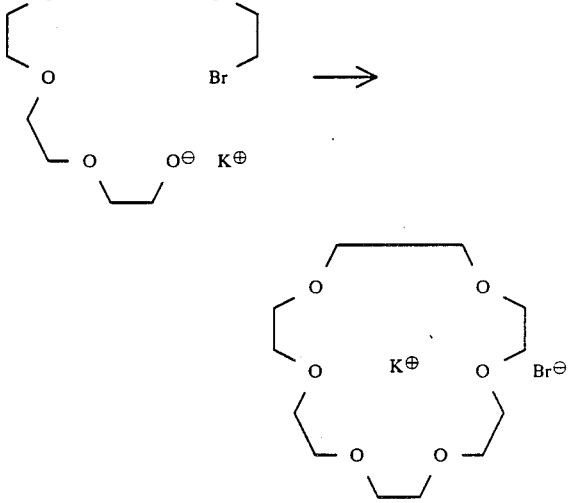

SUMMARY OF THE INVENTION

Accordingly, it is an object of the present invention to provide novel cyclic ester-amides useful in the production of materials such as crown-type ethers, without the disadvantages of some prior techniques that required high dilution procedures.

It is another object of the present invention to provide novel method for the production of useful new cyclic ester-amides.

Another object of the invention to provide a method for making these novel materials that is relatively straightforward.

In carrying out these and other objects of the invention, there is provided, in one form, method of producing novel cyclic ester-amides by reacting polyalkylene glycol monoamines with dicarboxylic acids and esters thereof in a molar ratio of about 1:1.

DETAILED DESCRIPTION OF THE INVENTION

We have discovered a new economical route to cyclic ether compounds that uses low cost starting materials. This approach is illustrated by the reaction between adipic acid and a polyethylene glycol monoamine having the formula NH$_2$—(CH$_2$CH$_2$O)$_x$—H, where x ranges from 2 to 5 to give a product such as the following:

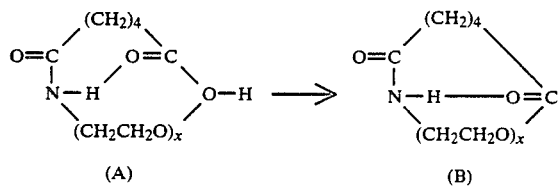

(A)  (B)

where it is believed that (A) is selectively formed and then serves as its own template to form (B). Adipic and pimelic acid are the preferred dibasic acids, and preferably with x in the monoamine formula being 2, 3 or 4, more broadly from 2 to 6. These cyclic products are along with higher molecular weight cyclic polyester amides. Glutaric acid yields mixtures of the cyclic imide with some cyclic polyether ester amide in the lower molecular weight fraction. Suberic acid and higher molecular weight dibasic acids yield polymers.

The compounds of the present invention may be defined, in one aspect, as having the following formula:

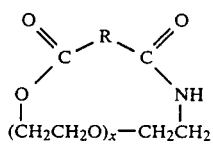

where R is an alkyl group having from 3 to 5 carbon atoms, and x ranges from 2 to 6

The polyethylene glycol monoamines that are produced as by-products in the production of JEFFAMINE® EDR amines. The by-products are materials such as triethylene glycol monoamine (TEGMA) and tetraethylene glycol monoamine (T$_4$EGMA) may be advantageously reacted with dicarboxylic acids to form novel cyclic ester-amides, which may be called in a preferred form, cyclic polyether ester-amides. The polyethylene glycol monoamine has the formula NH$_2$—(CH$_2$CH$_2$O)$_x$—H, where x ranges from 2 to 6, in one aspect x ranges from 2 to 5, and in a preferred aspect, x ranges from 3 to 4, which encompasses TEGMA and T$_4$EGMA. Although polyethylene glycol monoamines are preferred in one aspect of the invention, amino alcohols in general may be used, including other amino polyether alcohols from those discussed above, including, but not necessarily limited to, polyalkylene glycol monoamines such as:

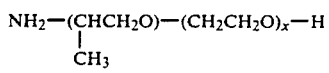

where x is one or greater, and

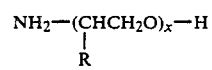

where x is greater than 1 and R is an alkyl group, such as methyl and ethyl, having from one to four carbon atoms.

The dicarboxylic acid is selected from the group of glutaric, adipic, pimelic acids and mixtures thereof. In one aspect, adipic acid and pimelic acid are preferred, with adipic acid being the most preferred. In one form, the dibasic acid may be defined as HOOC—R—COOH, where R is an alkyl group having from about 3 to 5 carbon atoms, where 4 to 5 carbon atoms is the most preferred. Esters of these acids may also be used.

Succinic anhydride as the carboxylic acid when R would have only 2 carbon atoms yields a cyclic imide as expected; illustrated in the reaction scheme below:

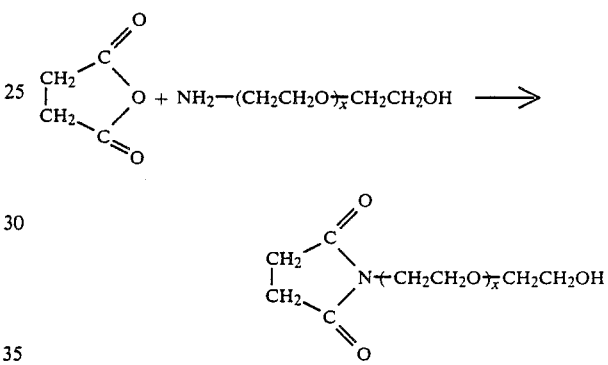

Glutaric acid, on the other hand, gives both the desired cyclic ether amide ester product and the cyclic imide:

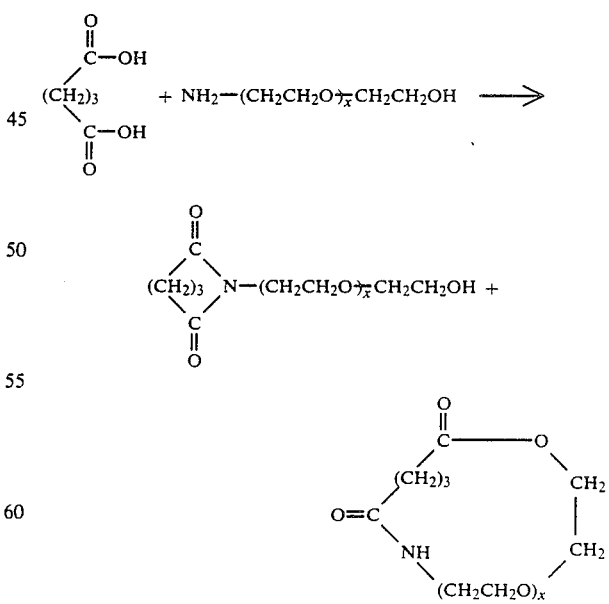

The molar ratio of polyethylene glycol monoamine to acid should be about 1:1 for these cyclic products. The reaction temperature may range between about 180° and 260° C., while pressures of 1 mm to several atmospheres may be used. Atmospheric pressure may be used, but a higher pressure is generally preferred. A catalyst may be optionally employed. Suitable catalysts include, but are not necessarily limited to, titanium alkoxides, Ti(OR)$_4$ where R is an alkyl radical having from 1 to 8 carbon atoms; zinc, antimony and manganese salts of carboxylic acids, and mixtures thereof. The products and methods of this invention will be described in more detail with reference to the following examples.

EXAMPLE 1

Reaction of Adipic Acid with Triethylene Glycol Monoamine

To a 250-ml, 3-necked flask equipped with a stirrer, thermometer and Dean-Stark trap was added 73.5 g. of triethylene glycol monoamine (0.49 moles). Then 73.5 g. of adipic acid (0.50 moles) was added portion wise. The mixture became viscous so 50 ml of methanol was added. The mixture was allowed to stir for one hour at 30°-40° C., then heat was applied. When the temperature reached 188° C., 11.8 ml of water was collected. After two hours at 200°-209° C., 14.8 g of water was obtained. The product was heated at 225°-246° C. at 0.35-0.55 mm. At this point the product had a hydroxyl number of 0, amine content of 0.02 meq./g. and an acid value of 0.6 meq./g. After further treatment of 50 g. of material at 220°-242° C. and about 0.04 mm for 1.2 hours, about 1 gram of adipic acid was collected overhead. It was felt that the product contained the cyclic product shown below along with higher oligomers. The product shown, 1,4,7-trioxa-11,16-dioxa-10-azacyclohexadecane, has some similarity to 16-crown-4 analog.

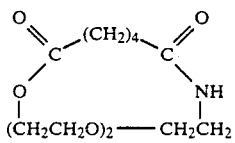

Analysis by NMR indicated a few percent of linear ester. The sample was run on GC/MS with only one large peak eluting. The highest mass in the spectral pattern was 259 which corresponds to the molecular weight of the cyclic structure.

EXAMPLE 2

Example 1 above was repeated using 372.5 g. of triethylene glycol monoamine (2.5 moles) and 365 g. of adipic acid (2.5 moles). The reactants were heated to 241° C. and 82 ml of water were collected. Then the product was heated at 200° C. at less than 2 mm for 1.5 hours. The product contained 0.01 meq.g. amine and 0.06 meq./g. hydroxyl content. Its average molecular weight by boiling point elevation using methanol was 1601.

EXAMPLE 3

Reaction of Pimelic Acid with Triethylene Glycol Monoamine

To a 100-ml, 3-necked flask equipped with a mechanical stirrer, nitrogen inlet and Dean-Stark trap was added 16.2 g. of pimelic acid and 14.9 g. of triethylene glycol monoamine. The flask was placed in a silicone oil bath and heated to remove water. After heating for two hours at 220° to 230° C. about 1.3 ml of water was removed. The contents were then heated to 200° C. and 0.5 mm for two hours. The product was a highly viscous semisolid containing very little hydroxy or amine groups (0.08 and 0.03, meq/g. respectively). NMR indicated cyclic products. GC/MSD showed the same fragmentation pattern as the product described in Example 1. The molecular weight obtained was 273.

EXAMPLE 4

Reaction of Adipic Acid with Tetraethylene Glycol Monoamine

To a 250-ml, 3-necked flask equipped with a thermometer, stirrer, Dean-Stark trap and nitrogen pad were added 73 g. of adipic acid and 96.5 g. of tetraethylene glycol monoamine. The contents were heated for two hours at 200° C. at which 11.8 ml of water was removed. The reactants were heated for an additional 1.5 hours at 240° C. where 15.5 ml of water were removed. Finally, the product was heated at 200° C. at about one mm. There was obtained 150.5 g. of soft brown solid which was flowable when heated. It was soluble in water and contained 0.02 meq/g. NH$_2$ and 0.1 meq/g. of hydroxyl. NMR and GPC and mass spectra analysis led to the conclusion that the cyclic product (MW=303) shown below was prepared:

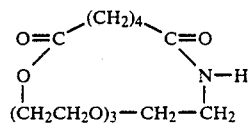

EXAMPLES 5

Reaction of Suberic Acid with Triethylene Glycol Monoamine

Suberic acid was heated with triethylene glycol monoamine in a manner described in Example 19. The product was a polyester polyamide with a molecular weight of about 5000. It had a melting point of 47° C. (TGA).

EXAMPLE 6

Reaction of Adipic Acid with Diethylene Glycol Monoamine

Adipic acid was heated with a diethylene glycol monoamine. The product was a clear yellow low melting solid with only a trace of hydroxyl and amino groups. The product was a solid with a molecular weight of 2000. It contained the product shown below:

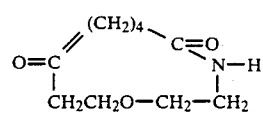

EXAMPLES 7-10

Reaction of Glutaric Acid with Diethylene Glycol Monoamine, Triethylene Glycol Monoamine and Tetraethylene Glycol Monoamine The reaction of glutaric acid with diethylene glycol monoamine (Diglycolamine ® Agent), triethylene glycol monoamine and tetraethylene glycol monoamine were rather inconclusive. It was felt that a mixture of cyclic product and imide compounds as shown below were obtained:

$$\text{(CH}_2)_3 \begin{array}{c} \text{C}=\text{O} \\ \diagup \quad \diagdown \\ \diagdown \quad \diagup \\ \text{C}=\text{O} \end{array} \text{N}-\text{(CH}_2\text{CH}_2\text{O)}_x-\text{H}$$

x = 2, 3 or 4

For that reason, the product from succinic anhydride and triethylene glycol monoamine was prepared. The infrared structure showed a typical imide linkage.

In GC/MSD each sample listed below in Table I as samples 1 through 4 show similar fragmentation patterns. Samples 5 through 8 show the same fragmentation patterns which are definitely different from samples 1 through 4.

TABLE I

Reactions of Dicarboxylic Acids with Polyethylene Glycol Monoamines

| Samp. | Reactants | Calc. MW for Amide/ esters | Obtained Mol. Wt. | Retention Time |
|---|---|---|---|---|
| 1 | Glutaric + DEGMA | 201 | 201 | 2.53 |
| 2 | Glutaric + TEGMA | 245 | 245 | 4.66 |
| 3 | Glutaric + T$_4$EGMA | 289 | 289 | 6.39 |
| 4 | Succinic + TEGMA | 231 | 231 | 4.2 |
| 5 | Adipic + DEGMA | 215 | 215 | 3.18 |
| 6 | Adipic + TEGMA | 259 | 259 | 5.38 |
| 7 | Adipic + T$_4$EGMA | 303 | 303 | 7.01 |
| 8 | Pimelic + TEGMA | 273 | 273 | 5.88 |

GC conditions: DBI 15 meter capillary column, 160 to 280° C. at 16° C./min. after one minute.

Many modifications may be made in the process of this invention without departing from the spirit and scope thereof which are defined only in the appended claims. For example, one skilled in the art may discover that particular reaction conditions or acids, which may not be explicitly recited herein, but which are nevertheless anticipated, would give desirable results.

We claim:

1. A method of producing novel cyclic ester-amides by reacting polyalkylene glycol monoamines with dicarboxylic acids and esters thereof in a molar ratio of about 1:1.

2. The method of claim 1 where the polyalkylene glycol monoamine has the formula $NH_2-(CH_2CH_2O)_x-H$, where x ranges from 2 to 6.

3. The method of claim 2 where x ranges from 2 to 5.

4. The method of claim 2 where x ranges from 3 to 4.

5. The method of claim 1 where the dicarboxylic acid is selected from the group consisting of glutaric, adipic, pimelic acids and mixtures thereof, and esters thereof.

6. The method of claim 1 where the dicarboxylic acid is selected from the group consisting of adipic acid, pimelic acid and mixtures thereof, and esters thereof.

7. The method of claim 1 where the dicarboxylic acid is adipic acid, and esters thereof.

8. The method of claim 1 where the reaction is conducted at a temperature between about 180° and 260° C.

9. The method of claim 1 where the reaction to produce the novel cyclic ester-amides employs a catalyst selected from the group consisting of Ti(OR)$_4$ where R is an alkyl radical having from 1 to 8 carbon atoms; zinc, antimony and manganese salts of carboxylic acids, and mixtures thereof.

10. A method of producing novel cyclic ester-amides having the formula:

$$\begin{array}{c} \text{O} \quad\quad\quad \text{O} \\ \diagdown\!\!\diagdown \quad\;\; \diagup\!\!\diagup \\ \text{C}-\text{R}-\text{C} \\ \diagup \quad\quad\quad \diagdown \\ \text{O} \quad\quad\quad \text{NH} \\ | \quad\quad\quad\quad | \\ (\text{CH}_2\text{CH}_2\text{O})_x-\text{CH}_2\text{CH}_2 \end{array}$$

where R is an alkyl group having from 3 to 5 carbon atoms, and x ranges from 2 to 6, by reacting a polyethylene glycol monoamine having the formula $NH_2-(CH_2CH_2O)_x-H$, where x ranges from 2 to 6 with at least one dicarboxylic acid, where the dicarboxylic acid is selected from the group consisting of succinic, glutaric, adipic, pimelic acids and mixtures thereof, including esters thereof, in a molar ratio of about 1:1.

11. The method of claim 10 where x ranges from 2 to 5.

12. The method of claim 10 where x ranges from 3 to 4.

13. The method of claim 10 where the dicarboxylic acid is selected from the group consisting of adipic acid, pimelic acid and mixtures thereof, including esters thereof.

14. The method of claim 10 where the dicarboxylic acid is adipic acid, including esters thereof.

15. The method of claim 10 where the reaction is conducted at a temperature between about 180° and 260° C.

16. The method of claim 10 where the reaction to produce the novel cyclic ester-amides employs a catalyst selected from the group consisting of Ti(OR)$_4$ where R is an alkyl radical having from 1 to 8 carbon atoms; zinc, antimony and manganese salts of carboxylic acids, and mixtures thereof.

17. Novel cyclic ester-amides having the formula:

$$\begin{array}{c} \text{O} \quad\quad\quad \text{O} \\ \diagdown\!\!\diagdown \quad\;\; \diagup\!\!\diagup \\ \text{C}-\text{R}-\text{C} \\ \diagup \quad\quad\quad \diagdown \\ \text{O} \quad\quad\quad \text{NH} \\ | \quad\quad\quad\quad | \\ (\text{CH}_2\text{CH}_2\text{O})_x-\text{CH}_2\text{CH}_2 \end{array}$$

where R is an alkyl group having from 3 to 5 carbon atoms, and x ranges from 2 to 6.

18. The novel cyclic ester-amides of claim 17 where R is from 4 to 5 and x ranges from 3 to 4.

* * * * *